United States Patent [19]

Lauer et al.

[11] Patent Number: 5,217,590
[45] Date of Patent: Jun. 8, 1993

[54] METHOD AND APPARATUS FOR THE INTRODUCTION OF A VOLUME OF AT LEAST ONE FLUID IN A TUBE IN PARTICULAR SUITABLE FOR CAPILLARY ELECTROPHORESIS SYSTEMS AND METHOD AND APPARATUS FOR SEPARATING AND/OR ANALYZING A FLUID MATERIAL

[75] Inventors: Hermanus H. Lauer, Drogteropslagen; Jan A. Ooms, Emmen; Marinus C. Hansen, Odoornerveen; Frederikus J. Logtenberg, Balkbrug; Karel A. Loth, Zwinderen, all of Netherlands

[73] Assignee: Lauer Labs B.V., Emmen, Netherlands

[21] Appl. No.: 757,850

[22] Filed: Sep. 11, 1991

[30] Foreign Application Priority Data

Sep. 11, 1990 [EP] European Pat. Off. ........ 90202412.4

[51] Int. Cl.$^5$ ................ G01N 27/26; G01N 27/447
[52] U.S. Cl. ................................ 204/180.1; 204/299 R
[58] Field of Search ............ 210/198.2, 656, 110, 210/659; 204/180.1, 182.8, 299 R

[56] References Cited

U.S. PATENT DOCUMENTS

| 4,470,910 | 9/1984 | Quemerais | 210/198.2 |
| 4,510,058 | 4/1985 | Cais | 210/198.2 |
| 4,906,344 | 3/1990 | Hjerten | 264/182.8 |
| 4,954,253 | 4/1990 | Alexandrov | 210/198.2 |
| 4,994,180 | 2/1991 | Sims | 210/198.2 |

FOREIGN PATENT DOCUMENTS

| 0329341 | 8/1989 | European Pat. Off. |
| 0339781 | 11/1989 | European Pat. Off. |
| 0383459 | 8/1990 | European Pat. Off. |

OTHER PUBLICATIONS

"Evaluation of an Automatic Siphonic Sampler for Capillary Zone Electrophoresis", S. Honda, et al, Journal of Chromatography, 404 (1987) 313–320, Chrom. 19 689, 1987 Elsevier Science Publishers B.V.

"Characterization and Automation of Sample Introduction Methods for Capillary Zone Electrophoresis", D. J. Rose, et al, 1988 American Chemical Society, Anal. Chem. 60 (1988) 642.

Primary Examiner—John Niebling
Assistant Examiner—John S. Starsiak, Jr.
Attorney, Agent, or Firm—Weingarten, Schurgin, Gagnebin & Hayes

[57] ABSTRACT

A method and apparatus for the injection of a quantitatively defined volume of at least one fluid into a tube or capillary, in particular suitable for capillary electrophoresis systems by immersing at least one end of the tube or capillary in the fluid to be injected in the tube or capillary and generating an overpressure in a space above the surface of the fluid to be injected, wherein said overpressure is generated by means of a syringe device comprising a cylinder and a piston movable in a controlled manner in the cylinder, said cylinder being filled with a suitable gas and being connected via a pressure line to said space above the surface of the fluid to be injected.

32 Claims, 4 Drawing Sheets

METHOD AND APPARATUS FOR THE INTRODUCTION OF A VOLUME OF AT LEAST ONE FLUID IN A TUBE IN PARTICULAR SUITABLE FOR CAPILLARY ELECTROPHORESIS SYSTEMS AND METHOD AND APPARATUS FOR SEPARATING AND/OR ANALYZING A FLUID MATERIAL

The present invention is concerned with miniaturized separation techniques and more in particular with automated methods for introducing samples into separation columns as for instance in capillary electrophoresis systems. These techniques are predominantly performed in narrow-bore columns such as capillaries that have an inner diameter preferably below 200 $\mu$m.

The miniaturization of separation techniques is driven by the following necessities:
- to analyze fractions of extremely small fluid sample volumes (microliter to sub microliter range) which would be strongly diluted in larger bore systems
- to use exotic (e.g. deuterated or highly pure) solvent systems to improve separation and/or detection of the species to be analyzed. The application of these types of solvent systems in larger bore systems is very expensive due to the large solvent quantities that are needed
- to hyphenate the separation technique with many types of detection or other analyzing systems that would not function properly when swamped with too much solvent
- to comply with environmental demands on the disposal of dangerous solvents or solvent combinations
- to observe stringent safety regulations in the laboratory.

In recent years significant advances have been made in micro-column separation techniques. Being able to analyze extremely small sample volumes has become exceedingly important with the explosion of research in the biological field, because often-times biological samples are quite small.

One of the significant problems with capillary techniques is in introducing the sample into the capillary in a precise and reproducible manner. One technique used is called sample injection by electromigration, an expression collectively including the effects of electrophoresis and electro-osmosis. In this known technique an end of the capillary and an electrode are placed into the sample and a voltage is briefly applied, causing a small band of sample to electromigrate into the capillary. This method of sample injection suffers from discrimination within the sample because solutes with higher mobilities will preferentially migrate into the electrophoresis column, and therefore change the relative composition of the sample.

To avoid this problem, attempts to physically inject sample have also been reported. However these direct injection techniques cause band broadening, apparently due to the laminar flow profile introduced during the injection.

The problem of introducing fractions of very small fluid samples in a precise and accurate manner into these miniaturized separation systems, without discrimination, has been more or less circumvented by those techniques that are able to generate accurate and precisely controlled pressure differentials over the separation column. These pressure differentials have been induced by:
1) gravity flow or siphoning, where fluid levels in the reservoirs at the inlet and outlet end of the connecting column are at controlled differential heights.
2) a constant vacuum or overpressure applied to the outlet or inlet of the connecting column.

The gravity flow or siphoning method has been discussed by S. Honda et al, Journal of Chromatography, 404 (1987), 313, and by D. J. Rose et al, Anal. Chem., 60 (1988), 642.

A vacuum method has been disclosed in EP-A-0329341.

There are, however, severe disadvantages with respect to sample introduction by the prior art differential pressure techniques, namely:

Gravity flow or siphoning is inaccurate and lacks precision in delivering accurate fluid volumes from small fluid reservoirs. In this type of reservoirs, surface forces between the sample fluid and reservoir wall will lead to uncertain positions of the fluid level. The latter will also change due to fluid withdrawal. These effects can only be neglected if both the original fluid volume is large with respect to the displaced volume and the height differential over time is known or constant. Furthermore, with this technique, it is impractical to deliver accurate fluid volumes in reasonable times in long and/or narrow diameter columns due to the very large difference in height of the fluid levels that is required.

With the vacuum technique or the overpressure technique the desired degree of the applied vacuum or pressure has to be precisely sensed and preserved by external means (e.g. a pump). This requires a feedback control system with sensing and regulating means for a predetermined pressure range in order to achieve the desired precision in the fluid metering. Also a larger range of injection pressures requires the availability of several sensing elements in order to cover the complete range of injection pressures.

The vacuum technique is akin to the siphoning technique in its inability to displace accurate fluid volumes in reasonable times in long and/or narrow diameter columns due to the limited pressure differential (typically not more than 1 bar) it can generate.

Although the overpressure technique is in principle not hampered by this limitation, it is nevertheless obvious that both techniques are inflexible due to the preset values of the pressure that have to be maintained precisely with mandatory hardware.

Another drawback of the vacuum technique stems from its possible failure sources such as: corrosion, gathering of dirt and degassing of the fluid when the vacuum is applied. This last failure source, in particular, can create bubbles in the connecting separation column which will cause severe field inhomogeneities during electrophoresis and a possible collapse of the current through the system.

EP-A-0339781 discloses an automated capillary injector for use in electrophoresis apparatus in which a sample is introduced from a sample vial into the capillary by connecting the vial to a source of constant fluid pressure. The pressure provided by the source of constant pressure need to be checked and, if necessary, adjusted. Thus pressure sensing devices connected in a feedback loop to the source of constant pressure as well as control apparatus for the source of constant pressure are necessary. Moreover, as in the known apparatus even a small leak in the pressurized part of the apparatus adversely influences the accuracy of the injector to a rather large degree, an integrator device integrating the area under the pressure curve with respect to time is provided, so that the amount of pressure can be accurately determined.

The present invention provides a method and apparatus that makes it possible to introduce samples of the kind needed for the above discussed microtechniques into a tube or capillary, without the problems inherent to the known techniques, and in a relatively simple, straight-forward and reliable manner.

According to the present invention a method for the injection of a quantitatively defined volume of at least one fluid into a tube or capillary by means of an overpressure is provided wherein said overpressure is generated by means of a syringe device comprising a cylinder and a piston movable in a controlled manner in the cylinder, said cylinder being filled with a suitable gas and being connected via a pressure line to said space above the surface of the fluid to be injected.

The present invention also provides an apparatus for injecting a quantitatively defined volume of at least one fluid into a tube or capillary, in particular suitable for electrophoresis systems, said apparatus comprising pressure generating means and means for receiving a fluid receptacle wherein the pressure generating means comprises a syringe device having a cylinder, a piston movable in the cylinder and drive means for the piston, said cylinder being connected by a pressure line to a pressure space in the means for receiving a fluid receptacle which space in use is sealed but is in open connection with the fluid in a receptacle.

The invention makes it possible to introduce a sample of fluid into a tube or capillary with a very high accuracy and precision in a rather simple and straight-forward manner. In addition thereto it is also possible to introduce two or more fluids into the tube after each other. This can sometimes be advantageous, when carrying out specific separation methods that require the presence of different fluids in the tube or capillary.

A very suitable method of applying a pressure at the end of the tube or capillary where the fluid must be introduced is using a stepping motor driving a syringe or piston within a cylinder. The advantage thereof is the very high accuracy, the precision and the short time within which the pressure can be built up, when using this system, without the necessity to use sensors to determine the pressure. This is especially important as such sensors are usually not sufficiently sensitive over the entire pressure range that can be applied. The use of a stepping motor eliminates this problem.

This actual pressure difference to be applied in a practical situation depends on the amount of fluid to be introduced, on the diameter and length of the tube and on the viscosity of the fluid. A person skilled in the art is able to determine this value by routine experiments. Suitable injection pressures may for instance be in the range from 0.001 bar up to 3000 mbar, more in particular from 0.001 bar up to 300 mbar for sample injection.

The tube or capillary to be used in the invention can be a conventional micro-technique capillary, having an internal diameter of up to 200 $\mu$m, preferably between 0.5 and 100 $\mu$m. It is however also possible to use the invention with tubes of other diameters, i.e. ranging from 0.1 $\mu$m to a few millimeters. The tube can have a circular inner shape, but it is possible to use other shapes, such as square, polyhedral or otherwise shaped channels.

The material of the tube depends on the system wherein it is to be used. Preferred materials are fused silica, quartz, glass, polymer or metal, optionally coated on the inside. Especially when used for chromatography, the tube may be provided with a coating effecting a separation or the tube may contain a packed bed of materials providing a separation of components of a sample.

The method of the invention can be used for any system wherein it is important to introduce quantitatively determined quantities of fluid, such as a liquid or supercritical fluid, into a tube or capillary. Examples of such systems are all kinds of quantitative analyses systems, like flow injection analysis, reaction systems to enhance the detection of reactants and preparative systems.

The invention can be used with all kinds of fluids for studying and/or separating their components or materials they may contain. The main restriction is found in the viscosity of the fluid. Fluids that are too viscous to be introduced into the tube cannot be used. The invention can be used to study molecular diffusion in hydrodynamic or electrophoretic systems and for the study of dispersion phenomena in general. It is possible to use different carrier fluids in the tube, which can be introduced accurately one after the other, or a combination of polar and apolar fluids. With these combinations one can improve the separations.

The carrier fluids that can be used within the scope of the present invention are in general electrolyte solutions (all kinds of ions in water), organic solvents, including solvent mixtures, supercritical fluids and water. Examples of suitable fluids are alcohols, acetonitrile, saturated hydrocarbons, unsaturated hydrocarbons, pure organic solvents spiked with conducting salts, e.g. lithium salts, or with receptor molecules, such as crown ethers, that may carry ions. One can also use supercritical fluids such as carbon dioxide and ammonia.

As sample fluids one can use fluids containing various kinds of components that one wants to study or separate. These components can be present in the same type of fluids as disclosed hereinbefore in relation to the carrier fluids or in other suitable fluids. Components to be separated by electrophoresis are in general all molecules or particles that can be dissolved or suspended in the carrier fluids and that may carry an effective net charge in those carrier fluids. Non limiting examples of components in aqueous solutions are ampholytes such as acids and bases, but also proteins, peptides, amino acids, polynucleotides and their constituents.

Examples of separation systems are chromatography, electrophoresis, and filtration systems, with or without applying a pH gradient. Accordingly the invention is also directed to a method of separating a fluid material comprising a mixture or solution of at least two components by chromatography, electrophoresis, or filtration, with or without applying a pH gradient in a tube, wherein the fluid is introduced into the said tube using the method described herein.

The invention is also directed to an apparatus for separating and/or analyzing a fluid material, comprising a mixture or solution of at least two components by chromatography electrophoresis, or filtration, with or without applying a pH gradient, said apparatus comprising a tube having an opening at each end, means for creating a pressure difference between said two openings, and means for obtaining a separation and/or analysis of the components of the fluid material. The apparatus may be provided with means for detecting at least one component of the fluid material.

In general all types of detection techniques can be used, including UV, VIS, fluorescence spectrometry and their indirect method, optionally in combination with laser techniques, mass spectrometry, conductivity, electrochemical detection, flame ionization detection (FID), infrared spectrometry and inductively coupled plasma (ICP).

Important advantages of the invention are not only the very easy, precise and accurate way in which the fluid can be introduced into the tube, but also the possibility to make the system symmetric, whereby it becomes possible to use combined separation techniques, such as chromatography, electrophoresis and filtration, which has the advantage that very specific separations can be obtained.

The invention will now be further explained with reference to the drawings of a preferred embodiment of an apparatus according to the invention.

Figure 1:
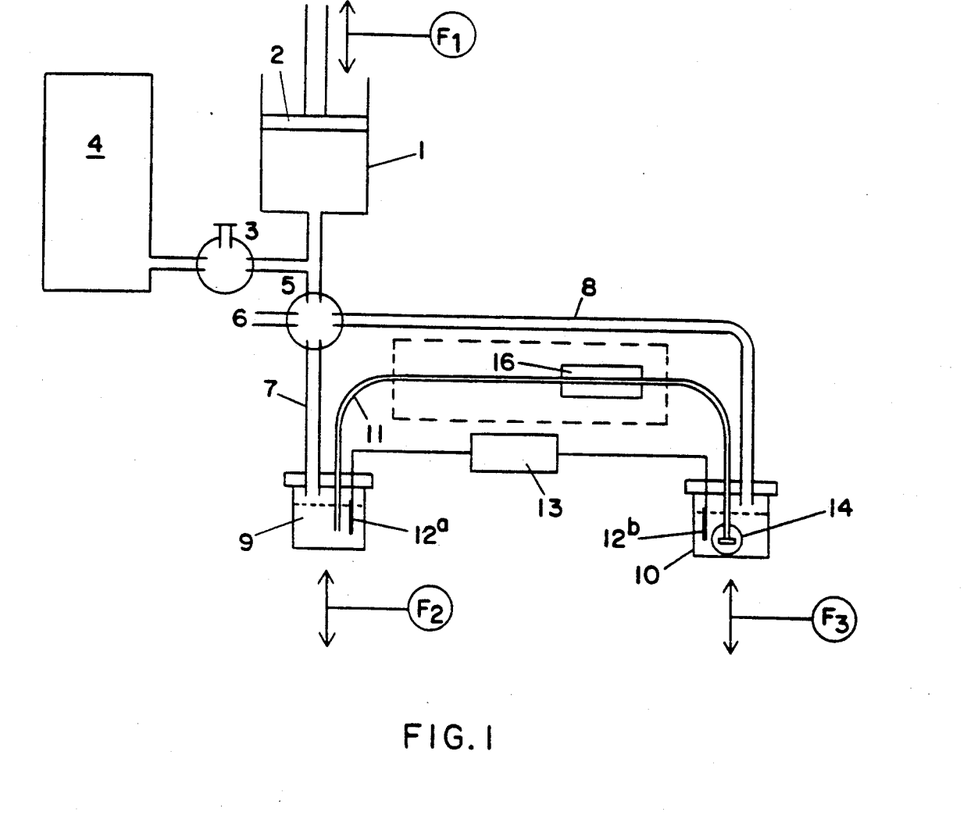
FIG. 1 diagrammatically shows an example of an apparatus for capillary electrophoresis embodying the present invention.

FIG. 1 diagrammatically shows by way of example an apparatus for capillary electrophoresis according to the invention comprising a vessel or cylinder 1 provided with a piston 2 and a piston displacement control means F1. Via a valve device 3, the vessel is connected to a buffer vessel 4, which has the advantage that the accuracy and precision are increased. The vessels 1 and 4, the piston and piston displacement control means and the valve device 3 together form a syringe device. Via multiport valve 5, the vessels are connected to lines 7 and 8. A vent 6 may be present but is not strictly necessary. Lines 7 and 8 terminate in fluid reservoirs 9 and 10 respectively. These fluid reservoirs are closed, but accessible for the lines 7 and 8, the capillary 11 and electrodes 12a and 12b. Adjacent or around the capillary a detector 16 is provided.

The reservoirs are provided with electrodes 12a and 12b, connected to a high voltage power supply 13 for moving in conventional manner a sample introduced in the capillary through the capillary. The outlet of the capillary in reservoir 10 may be provided with an outlet valve system 14 as will be discussed in more detail hereinbelow.

The reservoirs 9 and 10 are also provided with reservoir level control means F2 and F3, to provide exactly the same fluid level in both reservoirs, as otherwise a gravimetric flow may occur in addition to the flow induced by the pressure difference.

Figure 2:
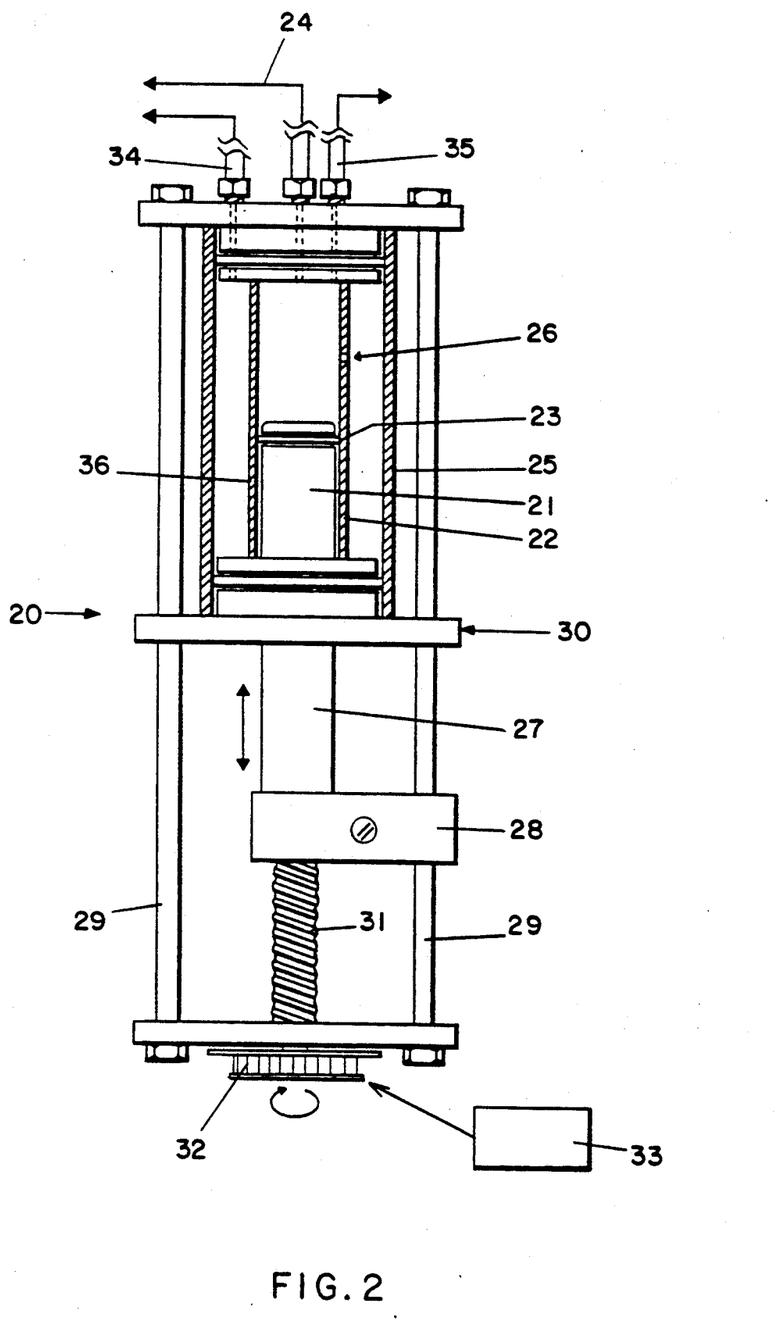
FIG. 2 diagrammatically shows an example of an embodiment of a syringe device according to the invention.

FIG. 2 diagrammatically shows a preferred embodiment of a syringe device 20 according to the present invention. The syringe device comprises a piston 21 placed in a cylinder 22. Sealing means have been schematically shown at 23. The piston may be moved up and down through the cylinder, which in use is filled with a suitable gas e.g. air or an inert gas. The cylinder is connected through a line 24 to a sample vial reception device shown in FIGS. 3 and 4. Thus when the piston is moved further into the cylinder the pressure at the sample vial reception device will increase.

The cylinder is connected to a buffer vessel, which in the embodiment shown is a barrel 25, placed concentrically around the cylinder 22. The barrel is connected to the cylinder by means of a simple bore 26 in the wall of the cylinder 22.

As long as the piston is below the level of the bore or hole 26 the barrel 25 acts as a buffer vessel. This means that a relative large piston displacement results in a rather small increase of the pressure in the cylinder and the buffer vessel and also in the sample vial. Thus the pressure can be controlled in a very accurate manner. As long as the piston is below the hole the pressure will be relatively low.

As soon as the piston seal 23 has passed the hole the buffer vessel is disconnected from the space above the piston. Then a small displacement of the piston has a rather large effect on the pressure in the cylinder, the line 24 and the sample vial, and a rather large overpressure can be generated. Such a high pressure is very suitable for flusing the capillary and for filling it with electrolyte before introducing a sample, but the high pressure range like the lower pressure range may be used for injecting a sample into the capillary.

The piston 21 has a piston rod element 27 extending through an end wall of the cylinder and connected to a support 28, which can slide along at least one guide rod 29. The at least one guide rod advantageously also is part of the frame 30 of the syringe device. Further in this embodiment the piston rod element or the support 28 is provided with a nut element (not shown) which engages a threaded drive rod 31. The drive rod in use is driven by a stepping motor 32. The stepping motor is energized and controlled by suitable control means 33, which may comprise for instance a microprocessor. A suitable stepping motor would be a stepping motor type MAE IIY 200 available from Mottori en Apparechiature Electriche which provides 200 steps per revolution.

The cylinder 22 and the barrel 25 may be made of any suitable material. In an experimental apparatus glass was used.

The drawing shows two pressure gauges 34,35 connected to the buffer vessel and the cylinder respectively. Those pressure gauges can be used for calibration purposes, and the high pressure gauge may also be part of a safety device. During normal use the pressure gauges generally are not used.

Thus in fact two discrete pressure systems are integrated in one unit:

1) a low pressure injection system (typical range 0–330 mbar) consisting of stepping motor, syringe system and buffer vessel; and
2) a high pressure system (typical 100–3000 mbar) particularly but not exclusively suitable for flusing consisting of the stepping motor and the syringe system but decoupled from the buffer vessel.

The disclosed syringe injection system is a dynamic system that is able to generate a virtually continuous and large range of pressures with a very high precision, which does not need a separate gas source. Valves are not needed. The concentric design eliminates temperature influences and the syringe system, capillary and sample vial may be regarded as a closed system so that Boyle's law is applicable.

In a preferred embodiment of the syringe system the piston rod element 27 and the hole in the end wall of the cylinder through which it extends allows gas flowing along the piston rod to and from the space under the piston and the gap between the piston and the cylinder, which gap 35 is present in the area below the piston seal. Thus, as soon as the piston seal has passed the hole 26 the buffer vessel via the gap and along the rod element is connected with the atmosphere and the pressure in the buffer vessel will become equal to the barometric value.

Moreover, preferably the piston seal and/or the hole 26 are designed in such a manner that a leak is created to vent the system including the vial and the capillary through the gap 35 and along the rod element 27 and equalize the pressure in the system, when the piston seal 23 is at the level of the hole 26. This position of the piston will advantageously be chosen during electrophoresis of a sample so as to prevent a possible increase of the pressure in the system due to a possible increase of the temperature. Thus undesired hydrodynamic flow profiles in the capillary during electrophoresis may be avoided.

Such a leak may simply be obtained by making the hole larger, at least in the direction of movement of the piston, than the thickness of the seal, that is the dimension of the seal in the direction of movement of the piston. The hole may then bridge the seal when the seal is exactly at the level of the hole.

With reference to FIG. 1 it is observed that line 8 is not necessary for injecting a sample in the tube or capillary 11. If line 8 is not present valve 5 may be omitted too. However via line 8 a counter pressure may be applied to a sample which has already been injected in the tube or capillary and which subsequently is being moved through the tube or capillary. Such a counter pressure may for instance be used to flatten out a curved flow profile of the moving sample.

Figure 3:
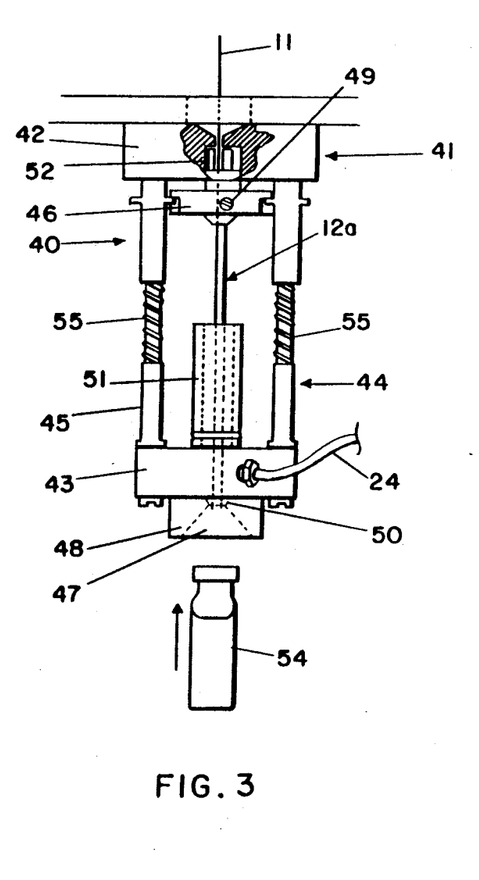
FIG. 3 and FIG. 4 diagrammatically show an example of the sample injection end of a capillary in an apparatus according to the invention in two different situations.
Figure 4:
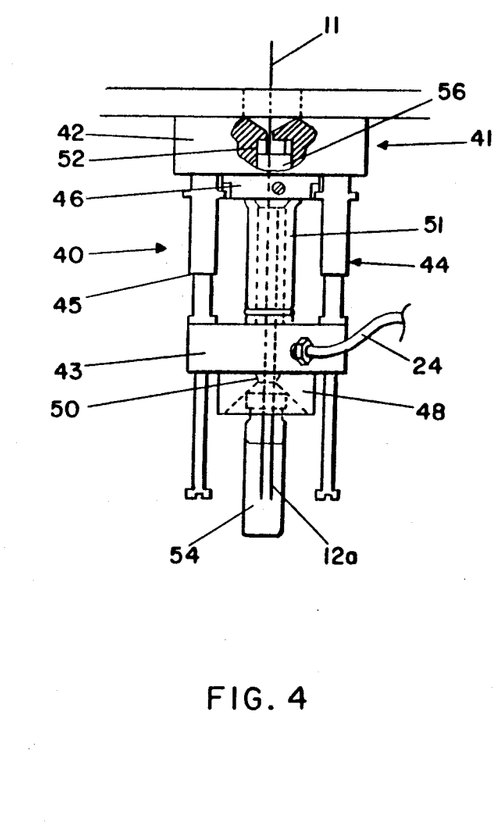

FIGS. 3 and 4 diagrammatically show an embodiment of a sample vial reception device 40 in the inoperative and operative state respectively. The sample vial reception device shown comprises a frame 41 having an upper box-like element 42 and a lower box-like element 43. The box-like elements are connected by two telescopic, springloaded arms 44,45. A tube or capillary 11 extends through the upper box-like element 42, through a cross-piece 46, connected below the box-like element 42 between the arms, and through the lower box-like element 43 into a cone shaped vial reception space 47 of a vial socket 48. The vial socket may be made from a suitable material like e.g. silicone rubber.

The cross-piece carries the electrode 12a which is connected by a screw 49 and which extends generally parallel to the capillary into the cone shaped vial reception space.

The lower box-like element 43 has an internal hollow space which is connected to the pressure line 24 from the syringe device, and which further through a bore in the top of the vial socket is connected to the inner space of a vial if a vial is present in the socket. Said bore preferably is the same bore through which the capillary and the electrode extend as indicated at 50 in FIGS. 3 and 4.

Sealing means 51 and 52 respectively have been placed around the capillary and electrode in between the box-like elements and around the capillary in the upper box-like element respectively.

The sealing means 51 and 52 both may each comprise a sleeve of flexible material e.g. a suitable silicone rubber. FIG. 3 shows the sealing means in the released state and FIG. 4 shows the sealing means in the tightened state.

The complete vial reception device functions in the following manner. Starting from the position shown in FIG. 3 a sample vial 54, which is first opened or has a seal which may be perforated by the capillary and the electrode, is moved towards the vial socket. The conical shape of the vial socket automatically positions the vial correctly and allows large variations in vial mouth diameter.

Once the vial is pushed firmly in the vial socket the springs 55 of the telescopic arms will be compressed and the lower box-like element will move towards the upper box-like element, until the sealing sleeve 51 touches the lower surface of the cross-piece 46.

Upon further pushing of the sample vial in an upward direction the cross-piece, which may move up and down over a small distance, will move towards the upper box-like element. An upper nose 56 of the cross-piece thereby compresses the sealing sleeve 52 and at the same time the sealing sleeve 51 is compressed.

Thus the sealing sleeve 51 seals at its upper and lower ends against the cross-piece and the lower box-like element. The sealing sleeve 52 is compressed and thereby tightens around the capillary so that any gas flowing from the pressurized space in the lower box-like element through the sleeve 51 and along the bore through which the capillary extends through the cross-piece is effectively blocked by the sleeve 52.

This sealed operative state in which pressure can be applied through the line 24 and in which the electrode 12a and the capillary extend into the sample vial 54 is shown in FIG. 4.

Of course when flushing the capillary the sample vial is replaced by a vial containing flushing liquid and the device functions in exactly the same manner. The pressure on the inlet fluid reservoir or sample vial is applied for a certain time which allows fluid to be displaced into the capillary according to Poiseuille's law of flow through a tube, $$F = \Delta p \pi d^4 / 128 \eta L \tag{1}$$

where F is the flowrate, or the volume displaced per unit time, $\Delta p$ the pressure difference (or overpressure) across the capillary with length L and internal diameter d and $\eta$ the viscosity of the bulk fluid in the capillary. The overpressure $\Delta p$ on the fluid level of the inlet vial is calculated from the piston movement and the dimension of the glass barrel and buffervessel by means of Doyle's law, $$P.V = \text{constant (at } T = \text{constant)} \tag{2}$$

where P is the absolute pressure, where V is the total volume of syringe, buffervessel, connecting lines and remaining gas volume over the fluid level of the inlet vial.

Although the absolute injection accuracy of this injection system theoretically will depend on many parameters such as, barometer value, vial size and fluid level, temperature drift of the system, compression and decompression effects, capillary diameter and length and viscosity of the bulk fluid in the capillary, they will hardly affect the injection precision due to the relatively short injection times.

Compression and decompression effects would cause major disturbances of the pressure profiles in the inlet vial if the system behaved adiabatically.

Figure 6:
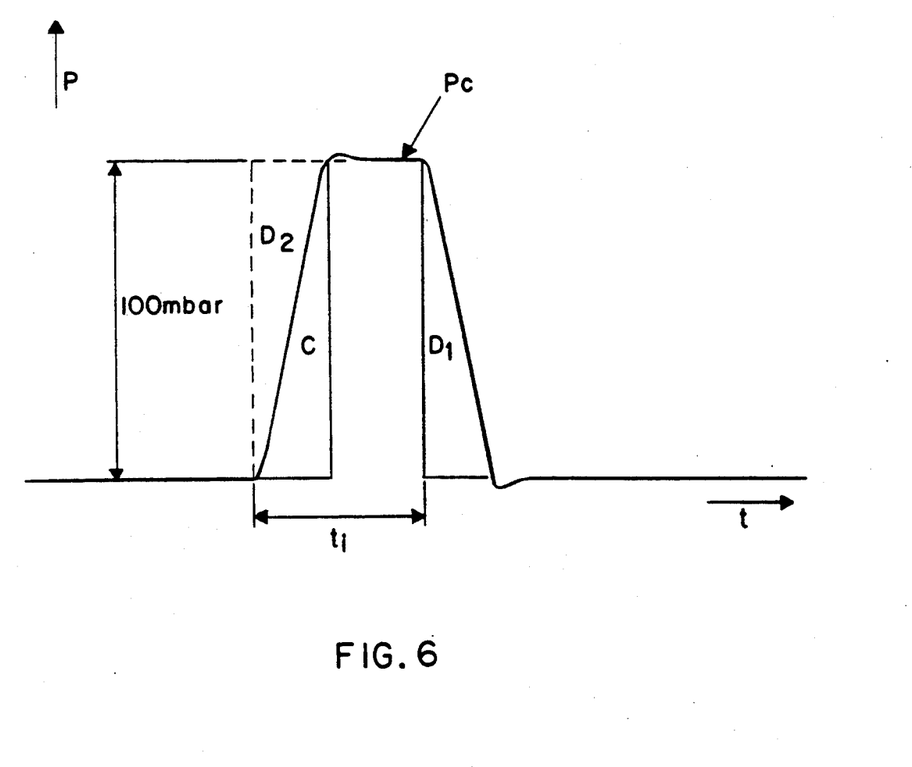
FIG. 6 shows a pressure-time diagram.

However, due to the small heat capacity of air and the good heat exchange to a steady state large heat capacity injection system, the compression and decompression pressure perturbations are relatively small and, on close inspection, cancel each other as is shown in FIG. 6 for a particular example. FIG. 6 shows a pressure-time diagram actually measured in an apparatus according to the present invention. Maximum pressure was 100 mbar and injection time ti was 6 seconds. When compression is chosen as the start of injection time and decompression as the end, the profile can be regarded as rectangular in Pt, if a pressure plateau Pc is reached, due to the near mirror images of the compression (C) and decompression (D1) phases of the profile as is shown in FIG. 6, wherein D1 substantially equals D2. For this reason equation (1) can still be applied without exact pressure sensing. The concentric design of pressure syringe and buffervessel avoids sudden temperature changes (PV/T) of the system as a whole as well as temperature fluctuations ($\Delta T$) in the separate volumes.

Vial size and fluid level are variables that affect the total gasvolume, but the relatively small size of the vials with respect to buffervessel+syringe has a negligible effect on exact pressure generation and can even be compensated for in software.

A larger buffer vessel produces a higher precision. Theoretically, the main error in this system will result from the determination of the start position of the piston. In order to be able to determine the position of the piston an optical detector and/or indicator may be present, for instance a pointer (not shown) connected to the support 28 and a scale (not shown) mounted on the frame 30.

According to a modification of the inventive apparatus a valve, as shown at 14 in FIG. 1, may be provided at one or both ends of the tube or capillary in order to shut or open the end(s) of the tube or capillary.

In FIG. 1 only at the outlet end of the capillary a valve has been provided. If the valve is closed the vial at the inlet end may be removed and/or exchanged for another one without the risk that siphoning occurs. Also the valve 14 makes it possible to first apply pressure at the inlet end of the capillary and then at a precisely determined point in time and/or a precisely determined duration start the injection of the sample by opening the valve 14.

There are various types of valves that can be used, like single-port or multi-port valves. Also a second tube sliding over the first one and closed at the free end and provided with an opening in a side wall can be used. It would even be possible to freeze the fluid in the tube or capillary locally.

Figure 5:
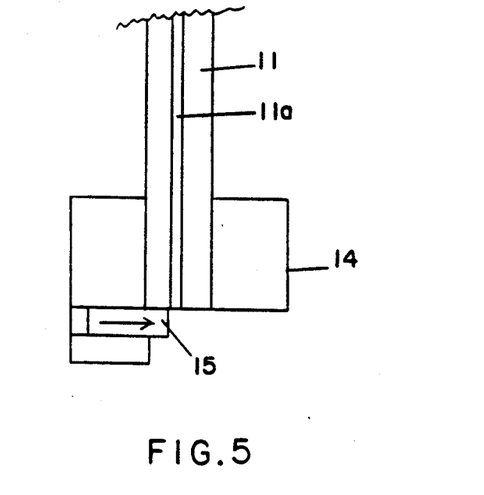
FIG. 5 diagrammatically shows an example of an embodiment of a detail of a modification of an apparatus according to the present invention.

FIG. 5 diagrammatically shows an embodiment of a valve 14 having a sliding element 15 which may be electromagnetically controlled and closes or opens the lumen 11a of the tube or capillary 11.

After a sample has been injected in the tube or capillary and after the valve 14, if present is closed again, the process can be repeated if desired with different samples and/or carrier fluids for a number of times. The pressure difference can be removed by opening the vent 6 via multiway valve 5.

After the sample has been introduced into the capillary, and fluid reservoir 9 has been reinstalled, a voltage is applied over the electrodes 12 for moving the sample(s) through the capillary and the composition of the sample can be detected in detector 16.

We claim:

1. A method for the injection of a quantitatively defined volume of at least one fluid into a tube or capillary, in particular suitable for capillary electrophoresis systems by immersing one end of the tube or capillary in the fluid to be injected in the tube or capillary leaving the other end thereof in an environment outside a space above the surface of the fluid to be injected and generating an overpressure in said space above the surface of the fluid to be injected, wherein said overpressure is generated by means of a syringe device comprising a cylinder and a piston movable in a controlled manner in the cylinder so as to inject a quantitatively defined volume of said at least one fluid into said tube or capillary, said cylinder being filled with a suitable gas and being connected via a pressure line to said space above the surface of the fluid to be injected, the cylinder being connected to a buffervessel.

2. A method as claimed in claim 1, wherein the movement of the piston is controlled by means of a stepping motor which in turn is controlled by a control means.

3. A method as claimed in claim 1, wherein the buffer vessel is placed concentrically around the cylinder and is connected to the cylinder by means of a hole in the wall of the cylinder.

4. A method as claimed in claim 3, wherein the piston is movable in a first section of the cylinder below the hole to provide a relatively low pressure, and in a second section beyond the hole to provide a relatively high pressure.

5. A method as claimed in claim 1, wherein after the injection of said at least one fluid, at least one second fluid is injected in similar manner.

6. A method as claimed in claim 1, wherein a first fluid is introduced into the tube or capillary at a high pressure, and subsequently at least one sample fluid is injected into the tube or capillary at a relatively low pressure.

7. A method for separating and/or analyzing a fluid material comprising a mixture or solution containing at least two components by chromatography, electrophoresis, or filtration, with or without applying a pH gradient in a tube, wherein the fluid is introduced into the said tube using the method of claim 1.

8. A method for the injection of a quantitatively defined volume of at least one fluid into a tube or capillary, in particular suitable for capillary electrophoresis by immersing at least one end of the tube or capillary in the fluid to be injected in the tube or capillary; closing the other end of the tube or capillary; generating an overpressure in a space above the surface of the fluid to be injected by means of a syringe device comprising a cylinder and a piston movable in a controlled manner in the cylinder, said cylinder being filled with a suitable gas and being connected via a pressure line to said space above the surface of the fluid to be injected; opening for a predetermined length of time the said other end of the tube or capillary so that said at least one fluid flows into the tube or capillary and closing the said other end again after said predetermined length of time, whereby a quantitatively defined volume of said at least one fluid is introduced in the tube or capillary, the cylinder being connected to a buffer vessel.

9. A method as claimed in claim 8, wherein the movement of the piston is controlled by means of a stepping motor which in turn is controlled by a control means.

10. A method as claimed in claim 8, wherein the buffer vessel is placed concentrically around the cylinder and is connected to the cylinder by means of a hole in the wall of the cylinder.

11. A method as claimed in claim 10, wherein the piston is movable in a first section of the cylinder below the hole to provide a relatively low pressure, and in a second section beyond the hole to provide a relatively high pressure.

12. A method as claimed in claim 11, wherein the syringe device is vented when the piston moves from the first section to the second section.

13. A method as claimed in claim 8, wherein after the injection of said at least one fluid, at least one second fluid is injected in similar manner.

14. A method as claimed in claim 8, wherein a first fluid is introduced in the tube or capillary at a high pressure and subsequently at least one sample fluid is injected in the tube or capillary at a relatively low pressure.

15. A method for separating and/or analyzing a fluid material comprising a mixture or solution containing at least two components by chromatography, electrophoresis, or filtration, with or without applying a pH gradient in a tube, wherein the fluid is introduced into the said tube using the method of claim 8.

16. An apparatus for injecting a quantitatively defined volume of at least one fluid into a tube or capillary, in particular suitable for electrophoresis systems, said apparatus comprising pressure generating means and means for receiving a fluid receptacle wherein the pressure generating means comprises a syringe device having a cylinder, a piston movable in the cylinder and precision drive means for moving the piston so as to inject a quantitatively defined volume of fluid, said cylinder being connected by a pressure line to a pressure space in the means for receiving a fluid receptacle which space in use is sealed but is in open connection with the fluid in a receptacle, and said cylinder of the syringe device being connected to a buffer vessel.

17. An apparatus as claimed in claim 16, wherein the buffer vessel is placed around the cylinder and is connected to the cylinder through a hole in the wall of the cylinder.

18. An apparatus as claimed in claim 17, wherein the piston has a sealing element and wherein the hole and the sealing element are designed to provide a leak past the sealing element if the sealing element is at the level of the hole.

19. An apparatus as claimed in claim 18, wherein the space below the sealing element of the piston is in connection with the atmosphere.

20. An apparatus as claimed in claim 15, wherein the piston has a piston rod extending through an end wall of the cylinder and being connected in driving relationship by a nut and threaded rod device to a stepping motor.

21. An apparatus as claimed in claim 20, wherein the stepping motor is connected to a control means for controlling the energization of the stepping motor.

22. An apparatus as claimed in claim 20, wherein the piston rod is provided with at least one support element, which is slidably connected to at least one guide rod extending substantially parallel to the threaded rod.

23. An apparatus as claimed in claim 15, wherein the means for receiving a fluid receptacle comprises a vial socket having a cone shaped vial reception space for receiving the mouth of a vial, said vial socket having at the top of the cone shaped space a bore connecting the cone shaped space with said pressure space.

24. An apparatus as claimed in claim 23, wherein the means for receiving a fluid receptacle have means for clamping an end section of a tube or capillary in such a manner that the tube or capillary in use extends through the bore of the vial socket.

25. An apparatus as claimed in claim 24, wherein the means for receiving a fluid receptacle has means supporting an electrode, wherein said electrode in use extends through the bore in the vial socket.

26. An apparatus as claimed in claim 23, wherein the means for receiving a fluid receptacle comprises a first box-like element connected by at least one arm to a second box-like element substantially parallel to said first box-like element, wherein said second box-like element is arranged to move along the at least one arm to and from the first box-like element between a nonoperative position and an operative position, and wherein the first box-like section is provided with means for clamping the tube or capillary while between the first and second box-like section a cross-piece supporting an electrode is provided.

27. An apparatus as claimed in claim 26, wherein said means for clamping the tube or capillary comprises a short sleeve of flexible material placed in the first box-like element around the tube or capillary, which sleeve in the operative position of the second box-like element is lengthwise compressed by a part of said cross-piece thereby tightening in a sealing manner around the tube or capillary.

28. An apparatus as claimed in claim 26, wherein between the second box-like element and the cross-piece a sleeve of flexible material is provided, which sleeve is placed around the tube or capillary and the electrode and is compressed lengthwise in the operative position of the second box-like element so as to provide a gastight seal between the cross-piece and the second boxlike element and around the tube or capillary and the electrode.

29. An apparatus as claimed in claim 17, wherein the cylinder has a first section for piston movement below the hole, and a second section beyond the hole, wherein the space above the piston is connected to the buffer vessel as long as the piston is in the first section, while the space above the piston is disconnected from the buffer vessel if the piston is in the second section.

30. An apparatus for separating and/or analyzing a fluid material comprising an apparatus for injecting a volume of fluid as claimed in claim 15 and a tube or capillary having an inlet end and an outlet end and detector means placed adjacent the tube or capillary, wherein at least at the outlet end of the tube or capillary a controllable closing means is provided for closing or opening said end of the tube or capillary at desired points of time.

31. An apparatus as claimed in claim 30, wherein said closing means comprises a sliding valve.

32. An apparatus as claimed in claim 30, wherein in said pressure line connecting the syringe device to said pressure space in the means for receiving a fluid receptacle, a multi way valve is provided which has a two connections connected to said pressure line and a third connection connected to a second pressure line, which second pressure line leads to a second pressure space at the outlet end of the tube or capillary, wherein the multi way valve in a first position is a through connection for the first pressure line and in a second position connects the syringe device to the second pressure line.

* * * * *

UNITED STATES PATENT AND TRADEMARK OFFICE
CERTIFICATE OF CORRECTION

PATENT NO. : 5,217,590  
DATED : June 8, 1993  
INVENTOR(S) : Hermanus H. Lauer

It is certified that error appears in the above-indentified patent and that said Letters Patent is hereby corrected as shown below:

Column 6, line 32, "flusing" should read --flushing--.

Column 6, line 66, "flusing" should read --flushing--.

Column 8, line 60, "buffervessel" should read --buffer vessel--.

Column 8, line 66, "buffervessel" should read --buffer vessel--.

Column 9, line 23, "Pt" should read --P-t--.

Column 9, line 30, "buffervessel" should read --buffer vessel--.

Column 9, line 34, "gasvolume" should read --gas volume--.

Column 9, line 35, "buffervessel" should read --buffer vessel--.

Column 10, line 29, "buffervessel" should read --buffer vessel--.

Column 12, line 12, "have" should read --has--.

UNITED STATES PATENT AND TRADEMARK OFFICE
CERTIFICATE OF CORRECTION

PATENT NO. : 5,217,590

DATED : June 8, 1993

INVENTOR(S) : Hermanus H. Lauer

It is certified that error appears in the above-indentified patent and that said Letters Patent is hereby corrected as shown below:

Column 12, line 58, "claim 15" should read —claim 16—.

Signed and Sealed this

Tenth Day of May, 1994

Attest:

BRUCE LEHMAN

Attesting Officer     Commissioner of Patents and Trademarks